US008858456B2

(12) United States Patent
Wood et al.

(10) Patent No.: US 8,858,456 B2
(45) Date of Patent: Oct. 14, 2014

(54) TRACHEA PRESSURE DETERMINATION METHOD AND DEVICE

(71) Applicant: Coviden LP, Boulder, CO (US)

(72) Inventors: Lockett E. Wood, Lyons, CO (US); Sarah Hayman, Boulder, CO (US); Youzhi Li, Longmont, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/081,156

(22) Filed: Nov. 15, 2013

(65) Prior Publication Data

US 2014/0081164 A1    Mar. 20, 2014

Related U.S. Application Data

(63) Continuation of application No. 12/477,636, filed on Jun. 3, 2009, now Pat. No. 8,603,003.

(51) Int. Cl.
| | |
|---|---|
| *A61B 5/08* | (2006.01) |
| *A61M 16/08* | (2006.01) |
| *A61M 16/00* | (2006.01) |
| *A61M 16/04* | (2006.01) |
| *A61B 5/00* | (2006.01) |
| *A61B 5/03* | (2006.01) |
| *A61B 5/085* | (2006.01) |

(52) U.S. Cl.
CPC . *A61B 5/036* (2013.01); *A61B 5/08* (2013.01); *A61M 2205/70* (2013.01); *A61M 16/0816* (2013.01); *A61M 16/0051* (2013.01); *A61M 2016/0027* (2013.01); *A61M 16/0434* (2013.01); *A61B 5/742* (2013.01); *A61M 16/0057* (2013.01); *A61M 16/044* (2013.01); *A61B 5/085* (2013.01); *A61M 16/0459* (2013.01); *A61B 5/7278* (2013.01)
USPC ......................................................... 600/529

(58) Field of Classification Search
USPC ......................................................... 600/529
See application file for complete search history.

(56) References Cited

U.S. PATENT DOCUMENTS

| | | |
|---|---|---|
| 3,931,822 A | 1/1976 | Marici |
| 4,285,340 A | 8/1981 | Gezari et al. |

(Continued)

FOREIGN PATENT DOCUMENTS

| | | |
|---|---|---|
| DE | 10213905 A1 | 10/2002 |
| WO | 9422518 A1 | 10/1994 |
| WO | 2010046874 A2 | 4/2010 |

OTHER PUBLICATIONS

Lomholt, N., A Device for Measuring the Lateral Wall Cuff Pressure of Endotacheal Tubes, Acta Anaesthesiologice Scandinavica, Dec. 1992, pp. 775-778, Issue 36.

(Continued)

*Primary Examiner* — Michael D'Angelo
*Assistant Examiner* — Christian Jang
(74) *Attorney, Agent, or Firm* — Fletcher Yoder PC (57) ABSTRACT

According to various embodiments, methods and systems for determining pressure in the lungs may employ intracuff pressure measurements. The intracuff pressure measurements may calibrated or adjusted based on a set of calibration coefficients or a set of calibration curves, which may reflect patient parameters and cuff/tube geometry factors. The resulting calibration may be used to determine a more accurate estimate of lung pressure, which in turn may be used to control a ventilator and provide breathing assistance to a patient. Also provided are tracheal tubes with couplers or other memory devices for storing calibration information. Such tubes may allow calibration at the level of an individual tracheal tube to account for changes in tube geometry and individual patient factors.

16 Claims, 10 Drawing Sheets

(56) References Cited

U.S. PATENT DOCUMENTS

| | | | |
|---|---|---|---|
| 4,526,196 | A | 7/1985 | Pistillo |
| 4,552,558 | A | 11/1985 | Muto |
| 4,565,194 | A | 1/1986 | Weerda et al. |
| 4,630,606 | A | 12/1986 | Weerda et al. |
| 4,898,168 | A | 2/1990 | Yule |
| 5,218,970 | A | 6/1993 | Turnbull et al. |
| 5,235,973 | A | 8/1993 | Levinson |
| 5,361,753 | A | 11/1994 | Pothmann et al. |
| 5,546,935 | A | 8/1996 | Champeau |
| 5,591,130 | A | 1/1997 | Denton |
| 5,740,796 | A | 4/1998 | Skog |
| 5,752,921 | A | 5/1998 | Orr |
| 5,819,723 | A | 10/1998 | Joseph |
| 5,885,248 | A | 3/1999 | Denton |
| 5,906,204 | A | 5/1999 | Beran et al. |
| 6,315,739 | B1 | 11/2001 | Merilainen et al. |
| 6,530,898 | B1 | 3/2003 | Nimkar et al. |
| 6,647,984 | B1 | 11/2003 | O'Dea |
| 6,820,618 | B2 | 11/2004 | Banner et al. |

OTHER PUBLICATIONS

Pollard, Richard J. MD et al., Endotracheal Tube Location Verified Reliably by Cuff Palpation, Anesthesia and Analgesia, 1995, pp. 135-138.

Cardoso, Monica M.S.C. MD et al., Portable Devices Used to Detect Endotracheal Intubation During Emergency Situations: A Review, Critical Care Medicine, May 1998, pp. 957-964, vol. 26, Issue 5.

Guttmann, Josef PhD et al., Continuous Calculation of Intratracheal Pressure in the Presence of Pediatric Endotracheal Tubes, Critical Care Medicine, Apr. 2000, pp. 1-21, vol. 28, Issue 4.

Karasawa, Fujio MD et al., Profile Soft-Seal Cuff, A New Endotracheal Tube, Effectively Inhibits an Increase in the Cuff Pressure through High Compliance Rather than Low Diffusion of Nitrous Oxide, Anesthesia and Analgesia, Dec. 2001, pp. 140-144, Issue 92.

Sondergaard, Soren et al., Direct Measurement of Intratracheal Pressure in Pediatric Respiratory Monitoring, Pediatric Research, Dec. 2002, vol. 51, No. 3.

Dullenkopf, A. et al., Air Leakage Around Endotracheal Tube Cuffs, European Journal of Anaesthesiology, Dec. 2004, pp. 448-453, Issue 21.

Horisberger, T. et al., Measurement of Tracheal Wall Pressure: A Comparison of Three Different in Vitro Techniques, Journal of the Association of Anaesthetists of Great Britain and Ireland, Dec. 2008, pp. 418-422, Issue 63.

Khazen, Vadim MD et al., Gastroesophageal Regurgitation during Anesthesia and Controlled Ventilation with Six Airway Devices, Journal of Clinical Anesthesia, Dec. 2008, pp. 508-513, Issue 20.

Orr, Joseph A., Tracheal Pressure Controller for Ventilators, National Institute of Allergy and Infectious Deseases, Jun. 2010, pp. 1-7.

International Search Report PCT/US2010/0036817, 5 pages, mailed Nov. 12, 2010.

TRACHEA PRESSURE DETERMINATION METHOD AND DEVICE

CROSS-REFERENCE TO RELATED APPLICATION

This application is a continuation of application Ser. No. 12/477,636, filed Jun. 3, 2009, entitled "Trachea Pressure Determination Method and Device" in the name of Lockett E. Wood et al., and assigned to Nellcor Puritan Bennett LLC, which is incorporated by reference herein in its entirety.

BACKGROUND

The present disclosure relates generally to medical devices and, more particularly, to airway devices, such as tracheal tubes.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea and into the lungs, for example during patient ventilation. Such tracheal tubes may include endotracheal (ET) tubes, tracheotomy tubes, or transtracheal tubes. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

To seal these types of tracheal tubes, an inflatable cuff may be associated with the tubes. When inflated, the cuff generally expands into the surrounding trachea to seal the tracheal passage around the tube to facilitate the controlled delivery of gases via a medical device (e.g., through the tube). For intubated patients, the flow rate and volume of gas transferred into the lungs, which may vary according to the condition of each patient, may be controlled by the settings of a ventilator. One factor that is used to determine the ventilator settings may be an airway pressure measurement, which is typically obtaining by measuring the pressure along the breathing circuit (e.g., medical tubing connecting the tracheal tube to the ventilator) at a point outside the patient. Airway pressure measured in the breathing circuit at a point outside the patient may be a useful surrogate for the pressure in the lungs, which may in turn be used for calculating a number of ventilator settings, for example settings involving pressure limits.

However, in circumstances where the internal diameter of the tracheal tube is diminished, for example through the buildup of mucosal secretions that may partially block the airflow passage of the tracheal tube, the lung pressure may be lower than the airway pressure measurement taken outside the patient. Accordingly, an airway pressure measurement may not always serve as a reliable substitute for lung pressure measurements.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Because direct measurements of the pressure in the internal space of the lungs is difficult, clinicians and respiratory specialists may use surrogate measurements of pressure along various points of breathing circuit or the patient's airway to estimate the lung pressure. The lung pressure estimates may then be used to determine the efficacy of the ventilation (e.g., the dynamic intrapulmonary compliance) and, in some cases, may be used to control the settings of a ventilator, either manually or automatically, to provide a clinical benefit to the patient.

Airway pressure may be estimated by using measurements of pressure taken along various points of the breathing circuit that are proximal to the tracheal tube. For example, such measurements may be used to assess a patient's work of breathing, which may include the airway resistance during movement of air into and out of the lungs. If the work of breathing of the patient increases, clinicians may assess whether the increase is due to increased airway resistance in the patient (e.g., stiffened lung tissue, which may be related to a clinical condition) or increased resistance in the tracheal tube due to buildup of biofilms on the inner diameter of the tube. Because airway pressure measurements taken proximal to the tracheal tube may not provide information about resistance built up distally, either in the patient or in the tube, trachea pressure measurements may provide information to the clinician about airway or tube-originated resistance. Trachea pressure may refer to pressure in the airway space below the cuff or near the distal tip of the cuff. With this information, when a patient's work of breathing increases, the clinician knows if it is due a change in the diameter of the tracheal tube or a change in the patient's respiratory system. If the resistance buildup is at least in part due to the tracheal tube, he may take action to suction secretions or increase the peak inspiratory pressure to overcome the increased resistance in the tracheal tube. If the work of breathing increase is due to the patient's respiratory system, he may deliver medication to the patient or change the ventilator settings. Tube-based increased work of breathing may be associated with patients who are relatively healthier than patients whose airway resistance has increased the work of breathing. Using such information may allow the clinician to more accurately assess when a patient is ready to come off of ventilator-assisted breathing.

In particular, because the internal diameter of tracheal tube may change during the time that the patient is intubated, for example through the buildup of patient secretions within the tube, measurements taken upstream of the tracheal tube in the breathing circuit may not be reliable for estimating pressure in the lungs. In certain embodiments, a measurement of tracheal pressure may be used as a surrogate for lung pressure or other pulmonary pressure measurements. The tracheal space is contiguous with the lung space, and tracheal pressure may be a more reliable measurement than measurements taken far upstream along the breathing circuit. Trachea pressure may be determined either directly with pressure transducers inserted at the distal end of the endotracheal tube or indirectly through measurements of pressure inside the cuff. Direct measurements may be difficult to obtain during long-term monitoring situations, because pressure transducers incorporated into the distal end of a tracheal tube may become covered in mucus or secretions, resulting in unreliable measurements.

Changes in tracheal pressure may be determined from changes in the interior cuff pressure ($P_{CUFF}$). Such determinations may exploit the relationships between changes in intracuff pressure and tracheal pressure, although they should account for the complexities of the relationship. The intracuff pressure may be changed by the pressure exerted on the underside of the cuff (e.g., against the annular area of the cuff between the trachea wall and the tube) during inhalation and exhalation. Cuffs with more surface area exposed to the trachea (i.e., around the tube) may be influenced differently than cuffs with less exposed surface area. The amount of surface area exposed to the sealed space in the trachea may influence the surface area exposed to the airway. Other factors that influence measured intracuff pressure may vary from cuff to cuff (e.g. manufacturing variability, cuff geometry, cuff materials) and patient to patient differences (e.g., trachea size).

Accordingly, the disclosed embodiments provide a more accurate method and system for determining trachea pressure by obtaining a measurement of pressure within the inflated cuff. This measured pressure may be used in conjunction with predetermined calibration values or predetermined calibration curves to estimate pressure in the lungs based on the intracuff pressure. Such calibration coefficients or curves may account for differences between various cuff sizes and geometries, which may be related to the amount of exposed surface area on the underside of the cuff. The resulting calibration may be used to determine a more accurate estimate of trachea pressure, which in turn may be used to control a ventilator and provide breathing assistance to a patient.

In certain presently contemplated embodiments, the calculated trachea pressure based on the intracuff pressure may be used to evaluate, adjust, or correct airway pressure values obtained along the breathing circuit or tracheal pressure values. For example, if the estimate of trachea pressure based on intracuff pressure varies significantly from the airway pressure measured upstream at a point closer to the ventilator, a clinician may be able to determine that the tracheal tube is blocked with secretions or other buildup, or that some other condition has developed, which may involve action by the clinician.

Also provided are tracheal tubes with couplers or other connectors including information elements, e.g., memory devices, for storing the calibration information or for providing information to an associated memory device relating to calibration. The tubes may be configured to communicate with appropriately configured (i.e., programmed) medical devices to access and use the calibration information in the determination of lung pressure. Such tubes may allow calibration at the level of an individual tracheal tube to account for changes in tube geometry and manufacturing variability factors. In addition, tracheal tubes may be provided with a primary inflation cuff that may be inflated to seal against the tracheal walls and one or more distal secondary calibration cuffs that may be used to determine the tracheal pressure.

In certain embodiments, the disclosed tracheal tubes, systems, and methods may be used in conjunction with any appropriate medical device, including a feeding tube, an endotracheal tube, a tracheotomy tube, a circuit, an airway accessory, a connector, an adapter, a filter, a humidifier, a nebulizer, nasal cannula, or a supraglottal mask/tube. The present techniques may also be used to monitor any patient benefiting from mechanical ventilation, e.g., positive pressure ventilation. Further, the devices and techniques provided herein may be used to monitor a human patient, such as a trauma victim, an intubated patient, a patient with a tracheotomy, an anesthetized patient, a cardiac arrest victim, a patient suffering from airway obstruction, or a patient suffering from respiratory failure.

Figure 1:
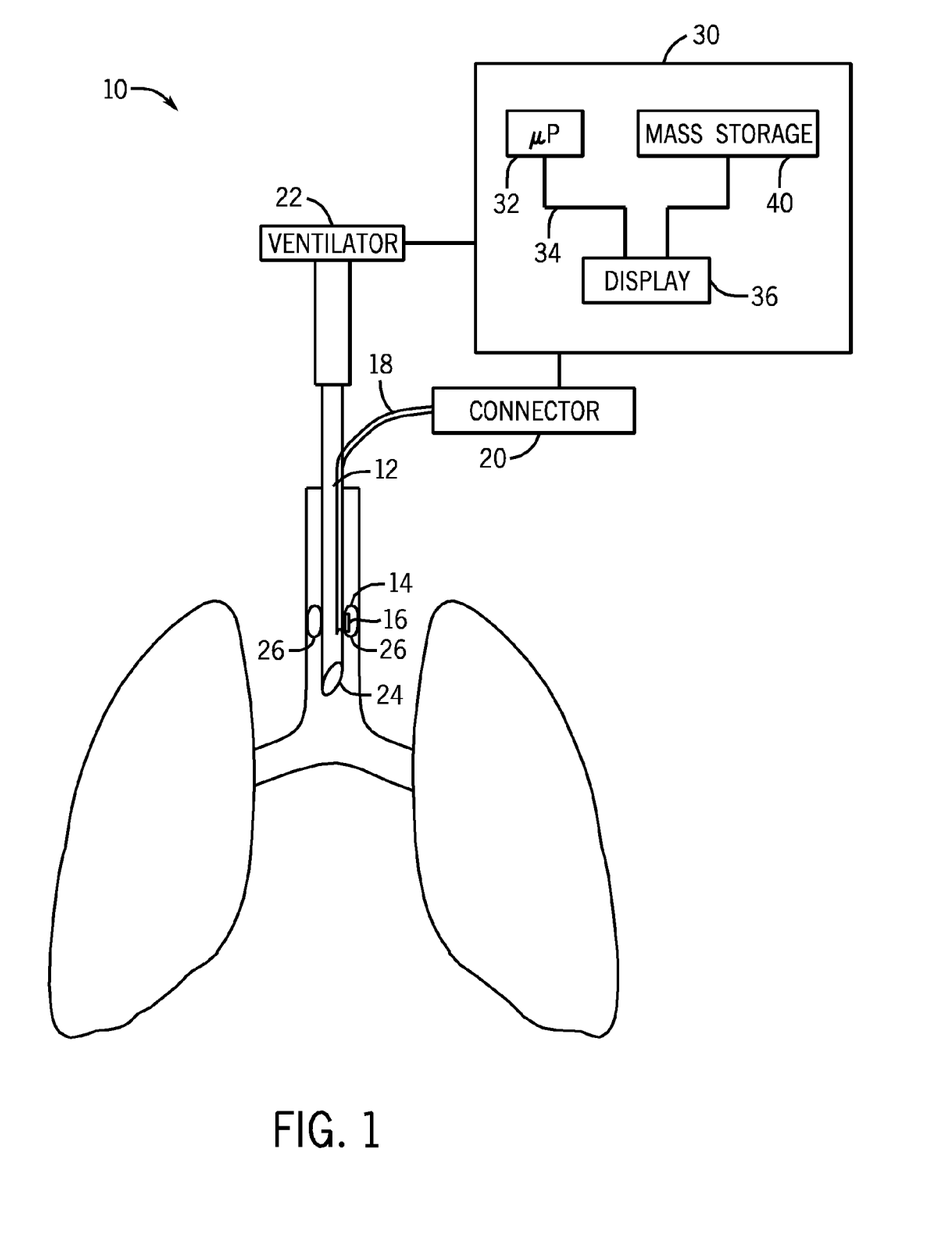
FIG. 1 illustrates a system including an endotracheal tube with a pressure transducer according to embodiments of the present techniques.

FIG. 1 shows an exemplary tracheal tube system 10 that has been inserted into the trachea of a patient. The system 10 includes a tracheal tube 12, shown here as an endotracheal tube, with an inflatable balloon cuff 14 that may be inflated to form a seal against the tracheal walls. The tracheal tube 12 may also include a pressure transducer 16 that is located within the inflated area of the cuff 14. In certain embodiments, the pressure transducer 16 may be coupled by a cable 18 to a connector 20 that may be coupled to a medical device, such as a ventilator 22 or a monitor 30. Fluids in the tracheal space 24 may exert pressure on the cuff 14, for example at an annular surface 26 of the cuff 14 that is exposed to the tracheal space 24. This in turn may influence the pressure measurements provided by the pressure transducer 16.

The system 10 may also include devices that facilitate positive pressure ventilation of a patient, such as the ventilator 22, which may include any ventilator, such as those available from Nellcor Puritan Bennett LLC. The system may also include a monitor 30 that may be configured to implement embodiments of the present disclosure to determine pressures based upon the pressure detected within the cuff 14 or another cuff. It should be understood that the monitor 30 may be a stand-alone device or may, in embodiments, be integrated into a single device with, for example, the ventilator 22.

The monitor 30 may include processing circuitry, such as a microprocessor 32 coupled to an internal bus 34 and a display 36. In an embodiment, the monitor 30 may be configured to communicate with the tube, for example via connector 20, to obtain signals from the pressure transducer 16. In certain embodiments, the connector 20 may also provide calibration information for the tube 12. The information may then be stored in mass storage device 40, such as RAM, PROM, optical storage devices, flash memory devices, hardware storage devices, magnetic storage devices, or any suitable computer-readable storage medium. The information may be accessed and operated upon according to microprocessor 32 instructions. In certain embodiments, calibration information may be used in calculations for estimating of pressure in the lungs. The monitor 30 may be configured to provide indications of the lung pressure, such as an audio, visual or other indication, or may be configured to communicate the estimated lung pressure to another device, such as the ventilator 22.

Figure 2A:
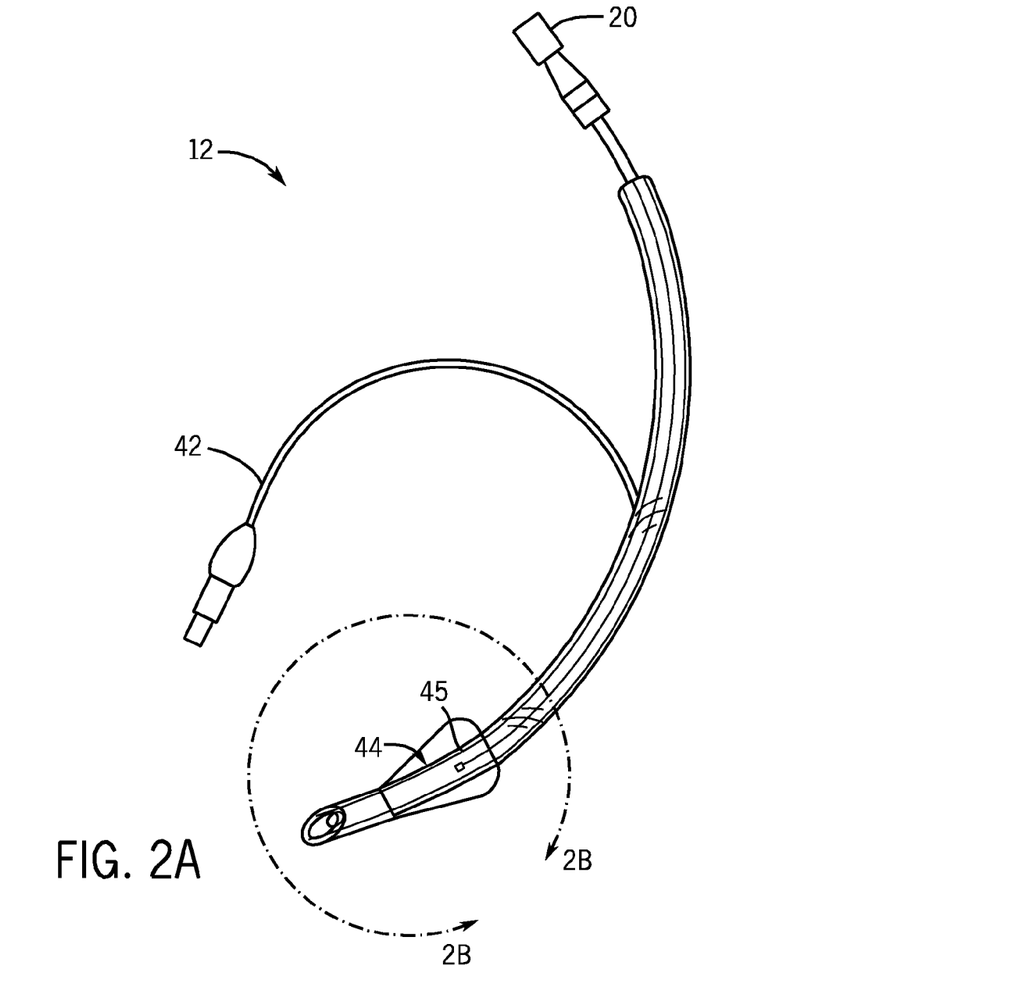
FIG. 2A is a perspective view of an endotracheal tube that may be used in conjunction with the system of FIG. 1 according to embodiments.

FIG. 2A is a perspective view of an exemplary tracheal tube 12 according to certain presently contemplated embodiments. The tube 12 may include a cuff 14 that may be inflated via inflation lumen 42. As shown in more detail in the detail view in FIG. 2B, the cuff 14 may define an inflated space 48 that substantially surrounds the pressure transducer 16, which may be embedded in or otherwise attached to an exterior surface 44 of a wall 45 of the tube 12. Leads 46 may connect the pressure transducer 16 to connector 20.

Figure 2B:
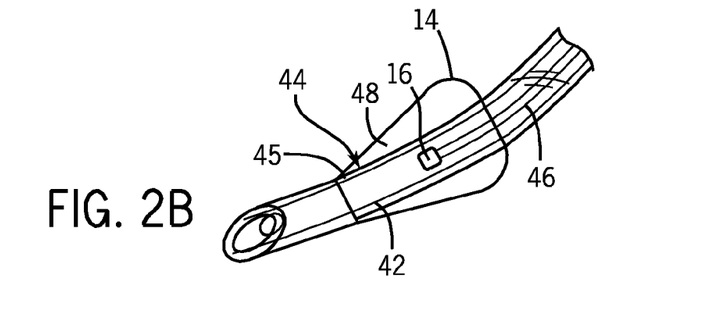
FIG. 2B is a detail view of the cuff area of the tube.

The pressure transducer 16 may be any suitable pressure sensor that may be integrated into or onto the exterior wall of the tube 12. For example, the pressure transducer 16 may be a piezoelectric pressure sensor. The leads 46 may be soldered or otherwise coupled to the pressure transducer 16 and may run along the length of tube 12 to connector 20 in any suitable manner. For example, the leads may be embedded within the wall 45 of the tube 12. In one embodiment, a lumen may be extruded into the walls 45 of the tube 12 into which the leads 46 may be inserted. It should be understood that, while the pressure transducer 16 may be integrated into or onto the exterior wall of the tube 12, other contemplated embodiments may involve a proximally located pressure transducer 16 that is in fluid communication, for example through a lumen, with the inflated area 48 of the cuff 12.

The connector 20 may be suitably configured to connect to a receiving port on the monitor 30. The connector 20 may contain an information element, such as a memory circuit, such as an EPROM, EEPROM, coded resistor, or flash memory device for storing calibration information for the cuff 14. The connector may also contain certain processing circuitry for at least partially processing signals from the pressure sensor or for interacting with any memory circuitry provided. When the connector 20 is coupled to the monitor 30, the information element may be accessed to provide cuff calibration information to the monitor 30. In addition, the connector 20 may facilitate providing pressure monitoring information to the monitor 30. In certain embodiments, the calibration information may be provided in a barcode that may be scanned by a reader coupled to the monitor 30. Alternatively, the pressure transducer 16 may include a passive or active RFID circuit that may be read wirelessly to convey pressure monitoring information and cuff calibration information to the monitor 30. In other embodiments, tube identifying data, calibration data, and so forth may simply be entered manually.

The tube 12 and the cuff 14 are formed from materials having suitable mechanical properties (such as puncture resistance, pin hole resistance, tensile strength), chemical properties (such as biocompatibility). In one embodiment, the walls of the cuff 14 are made of a polyurethane having suitable mechanical and chemical properties. An example of a suitable polyurethane is Dow Pellethane® 2363-80A. In another embodiment, the walls of the cuff 14 are made of a suitable polyvinyl chloride (PVC). In certain embodiments, the cuff 14 may be generally sized and shaped as a high volume, low pressure cuff that may be designed to be inflated to pressures between about 15 cm $H_2O$ and 30 cm $H_2O$. However, it should be understood that the intracuff pressure may be dynamic. Accordingly, the initial inflation pressure of the cuff 14 may change over time or may change with changes in the seal quality or the position of the cuff 14 within the trachea.

The system 10 may also include a respiratory circuit (not shown) connected to the endrotracheal tube 12 that allows one-way flow of expired gases away from the patient and one-way flow of inspired gases towards the patient. The respiratory circuit, including the tube 12, may include standard medical tubing made from suitable materials such as polyurethane, polyvinyl chloride (PVC), polyethylene teraphthalate (PETP), low-density polyethylene (LDPE), polypropylene, silicone, neoprene, polytetrafluoroethylene (PTFE), or polyisoprene.

Figure 3:
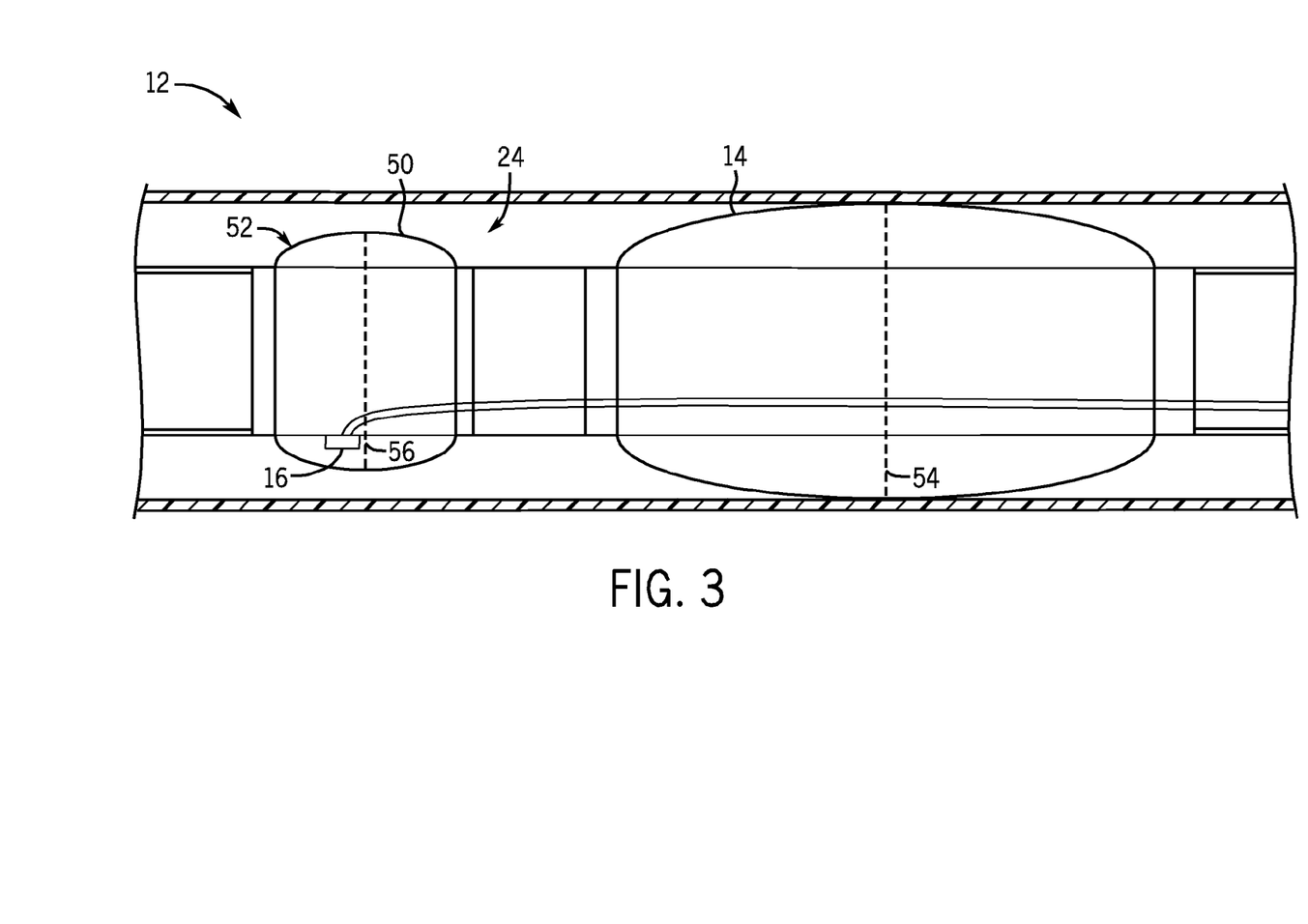
FIG. 3 is a perspective view of an endotracheal tube with a secondary inflation cuff that may be used in conjunction with the system of FIG. 1.

While the intracuff pressure may be measured within a cuff 14 that expands to form a seal against the tracheal walls of a patient, certain geometric properties of such a cuff 14 may be influenced by the anatomy of the patient. For example, depending upon the outer dimensions of the tube (i.e., the inner dimensions of the cuff), and the inner dimensions of the trachea, different areas of the surface 26 of the cuff may be exposed to the tracheal space 24. That is, the annular area of the cuff between the tube and the trachea may vary. To reduce the effect of patient anatomy variations on the intracuff pressure, an embodiment of a tracheal tube 12, as shown in FIG. 3, may include a secondary cuff 50 that may be suitably sized and shaped so that, when inflated, the walls 52 of the secondary cuff 50 may not touch the walls of the trachea. Accordingly, the geometry of the inflated secondary cuff 50 may be subject to little or no influence of the tracheal anatomy. The secondary cuff 50 may include a pressure transducer 16 that is capable of being coupled to the monitor 30 in the manner described above, either through connector 20 or through a wireless connection. When the secondary cuff 50 is inflated, the pressure in the tracheal space 24 may influence the sensed pressure within the secondary cuff 50.

When provided, the inflation volume of the secondary cuff 50 may be smaller than that of the cuff 14, which is large enough to meet the walls of the trachea when inflated. A typical sealing cuff 14 may be a high volume cuff configured to have a diameter 54 at a widest point about 1.5× the size of an average trachea, while the secondary cuff 50 may be configured to have a diameter at a widest point of about 0.5× or less than the size of an average trachea. For example, an adult trachea may range in size from 14 mm to 27 mm, with the average being around 20. Accordingly, a secondary cuff may have an inflated widest diameter 56 of less than about 10 mm, less than about 8 mm, or less than about 5 mm. In embodiments, various sizes of tubes 12 and cuffs 14 may be used for patients according to their physical characteristics. In one embodiment, the secondary cuff 50 may be sized up or sized down in proportion to the size of the tube 12. In one embodiment, because a calibration curve for a secondary cuff 50 may plateau above 40 cm $H_2O$, the cuff 50 may be inflated to 40 cm $H_2O$ or less in use, or between 40 cm $H_2O$ 20 and 60 cm $H_2O$, which corresponds to the area of the plateau. In other embodiments, the secondary cuff 50 may be inflated to any suitable pressure, for example between about 10 cm $H_2O$ and about 60 cm $H_2O$, to obtain pressure readings.

As noted, the secondary cuff 50 may experience reduced effects of patient anatomy on intracuff pressure, which in turn may reduce patient to patient variability in tracheal pressure effects on the intracuff pressure. In one embodiment, a tube 12 may include a primary sealing cuff 14 with a first pressure transducer 16, and secondary cuff 50 with a second pressure transducer 16. In such embodiments, the intracuff pressure of the secondary cuff 50 may be used to calibrate the effects of individual patient anatomy on the primary cuff 14. For example, both the primary cuff 14 and the secondary cuff 50 may be inflated to the same initial intracuff pressure (e.g., 25 cm $H_2O$). Any subsequent differences between the intracuff pressure between the primary cuff 14 and the secondary cuff 50 may be at least in part attributable to patient anatomy effects. In certain embodiments, the secondary cuff 50 may be only intermittently inflated to initially calibrate primary cuff 14 and then for spot checks of the calibration.

Figure 4:
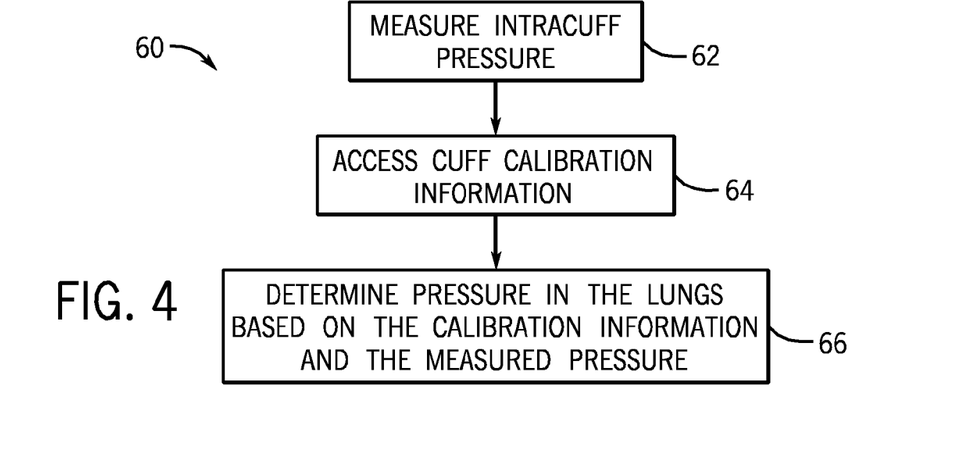
FIG. 4 is a flow diagram of an exemplary method for deriving pressure values.

FIG. 4 is an exemplary process flow diagram illustrating a method for determining trachea pressure based upon cuff pressure. The method is generally indicated by reference number 60 and includes various steps or actions represented by blocks. It should be noted that the method 60 may be performed as an automated or semiautomated procedure by a system, such as system 10. Further, certain steps or portions of the method may be performed by separate devices. For example, a portion of the method 60 may be performed by a pressure transducer 16, while a second portion of the method 60 may be performed by a monitor 30. In embodiments, the method 60 may be performed continuously or intermittently for long-term patient monitoring or at any appropriate interval depending on the particular situation of the intubated patient.

According to a presently contemplated embodiment, the method 60 begins with a measurement of intracuff pressure at step 62 by a transducer 16 associated with a tracheal tube 12 that has been inserted into a patient. The pressure may be communicated to the monitor 30 for further analysis. At step 64, the monitor also receives calibration information from an information element or other storage device associated with the connector 20. It should be noted that the monitor may, of course, receive data or signals directly from the pressure transducer. At step 66, trachea pressure is estimated from the intracuff pressure calibrated based on the calibration information.

As noted, the relationship between the intracuff pressure and the tracheal pressure may be used to estimate the trachea pressure. For example, a trachea pressure value may be determined by the relationship:

$$P_{TRACHEA}=f(P_{CUFF})$$

where the trachea pressure is a function of the pressure in the cuff. In one embodiment, the function may be solved to yield a calibration factor, r, that represents the "gain" of the individual cuff (e.g., cuff 14 and/or secondary cuff 50) and $P_{CUFF}$ is the monitored (e.g., sensed) intracuff pressure as measured by the pressure transducer 16. In one embodiment, r may be a ratio that defines the relationship between sensed cuff pressure peak to peak and trachea pressure peak to peak, where the peak to peak measurements are taken at a peak pressure of the respiratory cycle. The value of the coefficient r may be determined during a calibration phase of deployment of the tube, or may be a known value or set of values determined for individual tubes, cuffs, or tube products incorporating specific tube and cuff dimensions and materials. As noted above, such values may be automatically acquired from the tube (e.g., from information stored in the connector), or may be entered by scanning a barcode, or by manual input. Other techniques for determining such values may include referencing from a lookup table stored in the tube connector or in the monitor or ventilator, or even remote from these (e.g., in a network-accessible device).

Figure 5:
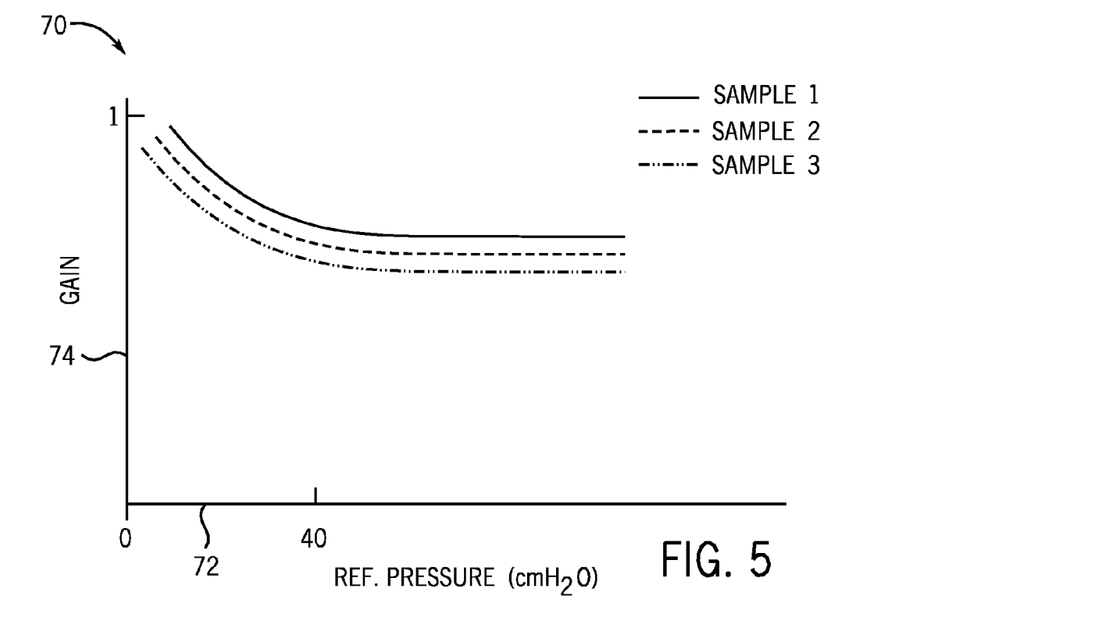
FIG. 5 is a plot of exemplary calibration curves for a set of cuffs.

In one embodiment, the $P_{CUFF\ (REFERENCE)}$, which may be the initial inflation pressure in the cuff or a reference pressure measurement taken at a minimum pressure point in the respiratory cycle, may be used to determine which coefficient r to select from a calibration curves for an individual cuff. Because the pressure exerted on the cuff from the trachea may change over the respiratory cycle of inhalation and exhalation, the $P_{CUFF\ (REFERENCE)}$ may represent the minimum pressure exerted on the cuff after exhalation. The $P_{CUFF\ (REFERENCE)}$ may be a rolling average of a minimum pressure during a predetermined number of peaks (e.g., five peaks). Because the pressure in the cuff may also change as a cuff moves within the trachea, using the $P_{CUFF\ (REFERENCE)}$ as a reference point may account for such orientation and/or movement effects on the cuff. For example, FIG. 5 is a plot 70 that shows examples of calibration curves for a set of cuffs of the same geometry. The $P_{CUFF\ (REFERENCE)}$ on the x-axis 72 is plotted against the gain r. As shown in FIG. 5, the y-axis 74 may be plotted against 1/r, from which r may be determined. By using the $P_{CUFF\ (REFERENCE)}$ that corresponds to the particular cuff being used, the coefficient r may be determined. The coefficient r may then be used to determine a ratio relationship for the trachea pressure and the monitored pressure in the cuff. In one example, the $P_{TRACHEA}/P_{CUFF}$ ratio, or the gain factor r, may be 1.2 Accordingly, for a monitored intracuff pressure of 30 cm $H_2O$, the Trachea pressure achieved in the lungs may be 36 cm $H_2O$. In a presently contemplated embodiment, for example, the trachea pressure may be a function of the initially detected cuff pressure, which may be considered as an offset value, and the continuously or periodically determined cuff pressure, such as by the relationship:

$$P_{TRACHEA}=rP_{CUFFs}-P_{CUFF\ (REFERENCE)}$$

wherein $P_{TRACHEA}$ is the trachea pressure, $P_{CUFFs}$ is the cuff pressure sensed, and $P_{CUFF\ REFERENCE}$ is an offset reference cuff pressure taken either right after inflation or right after a breath cycle, and r is the calibration ratio of sensed trachea pressure to cuff pressure (which, again, may be a fixed or varying value).

In practice, a series of relationships, which may be considered as "gain" surfaces, may be defined in advance for a particular tube and cuff combination, where each surface may be considered as "gain" curves. Each such combination may be presented as a tube product available for use by a physician or technician. The gain curves may establish relationships between the cuff pressure and the trachea pressure, and may be stored and accessed in any suitable manner, such as those discussed above. These curves may be derived from data such as that represented in FIG. 5. Based upon the initially detected cuff pressure, then, one of these curves or relationships is selected from among several available for an individual tube and cuff combination. This selection, then, may determine the coefficient r used subsequently to determine trachea pressure from measured cuff pressure. In certain embodiments, this process may be simplified by simplification of the relationship defining the "gain" coefficient (e.g., assigning a fixed value, linearization of non-linear relationships, and so forth). In certain cases it may also be possible to use a single coefficient for a tube product, and thus avoid selection of the gain relationship upon initial intubation.

It should also be noted that in alternative embodiments, such as those using a tube with a secondary cuff of the type described above, the process for trachea pressure determination may be further simplified. For example, in certain cases, the transducer within a secondary cuff that does not contact the trachea walls may be considered to represent the actual trachea pressure (or airway pressure) at the location of the cuff offset by an inflation pressure of the secondary cuff. That is, the pressure read by a transducer within the secondary cuff may be a sum of the cuff pressure and the pressure exerted on the cuff by the air in the surrounding airway. However, even when such secondary cuffs are employed, the actual airway pressure may be attenuated somewhat by the mechanical operation of the cuff, and a "gain" relationship may nevertheless be employed, as summarized above, to provide a more accurate estimation of the airway pressure.

Monitor 30 may use the estimated trachea pressure to determine whether the breathing system 10 is achieving compliance. In certain embodiments, the estimated trachea pressure may be used to correct or adjust settings on a ventilator 22. For example, compliance may be associated with achieving target pressures in the airway during ventilation. If the target pressures in the airway are not achieved, the ventilator settings may be adjusted to increase or decrease the inspiratory pressure. Further, the estimated trachea pressure may be used to determine whether there is a blockage along the tube 12 by calculating the tube resistance using the pressure measurements and flow measurements taken at points closer to the ventilator 22, where a resistance increase may be indicative of a blockage or change in diameter of the tube 12. The monitor 30 may be configured to provide a graphical, visual, or audio representation of the estimated lung pressure. For example, ventilation compliance may be indicated by a green light indicated on a display, while a drop in pressure indicating a blockage in the tube 12 may trigger an alarm, which may include one or more of an audio or visual alarm indication. In one embodiment, the alarm may be triggered if the change in pressure is substantially greater than a predetermined value, substantially less than a predetermined value, or outside of a predetermined range.

Figure 6:
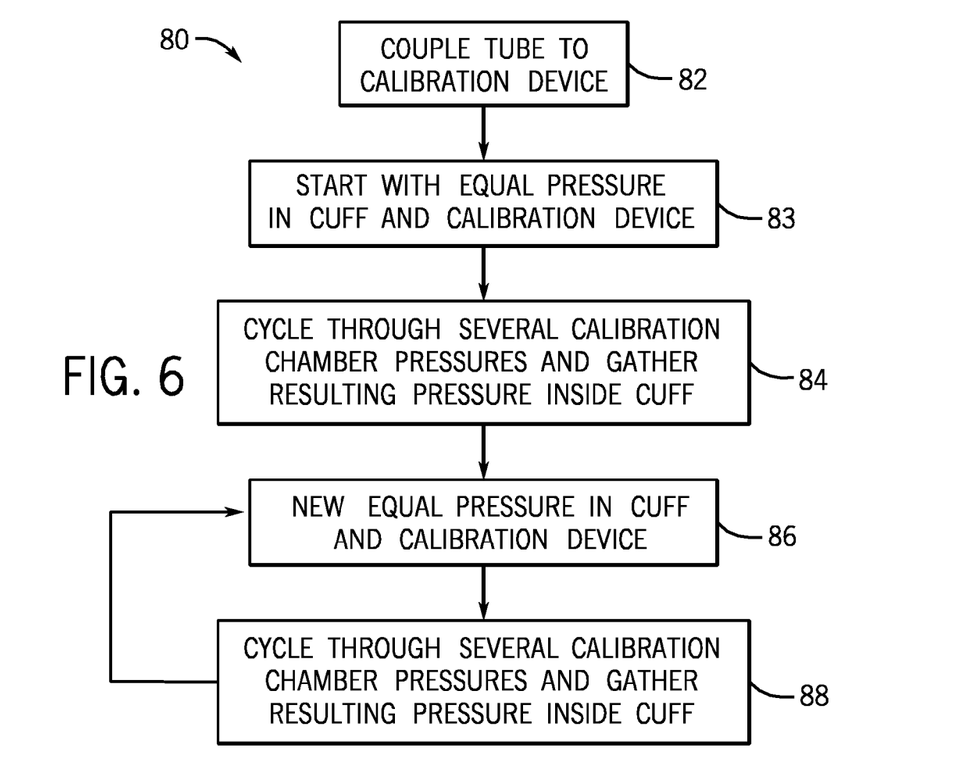
FIG. 6 is a flow diagram of another exemplary method for deriving calibration factors for a method involving measuring pressure through a secondary cuff.

The information encoded on an information element, for example associated with the connector 20, may be encoded during a tracheal tube manufacturing process. FIG. 6 is a process flow diagram illustrating a method for determination of such information, for example in conjunction with a secondary cuff 50. The method is generally indicated by reference number 80 and includes various steps or actions represented by blocks. At step 82, a tracheal tube is coupled to a device that inflates the attached cuff 50 over a series of inflation pressures. The device may include a pneumatically sealed chamber or other surrogate for determining the pressure in the space outside the cuff. At step 83, the cuff 50 and the device may be set so that the pressures are substantially equal. At step 84, the pressure in the calibration device is cycled (e.g., incrementally) through a range of pressures (for example, ranging from about 20 to about 100 cm $H_2O$) while the pressure inside the cuff is measured during the cycling.

At step 86, the cuff is inflated to a new equal pressure with the calibration device (e.g., an increment of 5 cm or 10 cm $H_2O$ greater than the pressure used at step 83). Pressure measurements inside the cuff are taken while the calibration device is cycled through a range of pressures at step 88. Steps 86 and 88 may be repeated any number of times with different cuff pressures used each time. A secondary cuff 50 may be inflated up to 60 cm $H_2O$, in particular because the cuff 50 does not contact the trachea walls, so higher inflation pressures relative to a sealing cuff 14 may be used. In this manner, the cuff 50 may be calibrated for a range of pressures inside the cuff as well as for a range of trachea pressures.

Figure 7:
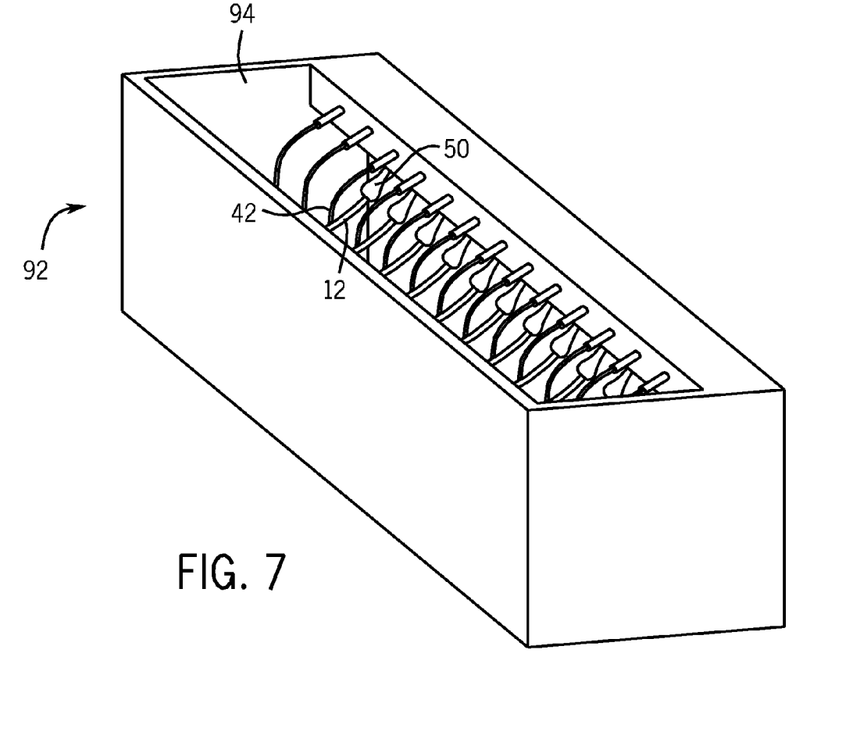
FIG. 7 is a perspective partial cutaway view of a calibration structure for lung pressure determination.

FIG. 7 is a perspective partial cutaway view of an example of such a calibration chamber 92. The calibration chamber may define a space 94 that may be enclosed and kept at a known pressure. One or more tracheal tubes 12 may be installed within the space. The cuffs 50 may be inflated via inflation lines 42 to a series of pressures. At step 86, the pressure inside the cuff 50 may be monitored and, at step 88, the relationship between the known pressure in the space 94 and the sensed pressure for an individual cuff 50 may be determined or, alternatively may be stored as raw data for subsequent processing or analysis. The relationship information over a series of cuff pressures may be stored on a memory circuit associated with the tube 12 (or otherwise, as described above), as indicated at step 90. In such an arrangement, the relationship between cuff pressure and outside pressure may be determined on an individual tube basis. Similar calibrations may be made for products or families of tubes, such as by size, or by combinations of particular tubes and cuffs. By obtaining information about the r factor for different tracheal pressures as well as intracuff pressures, r may be extrapolated even in situations were the calibration factor is non-linear.

Figure 8:
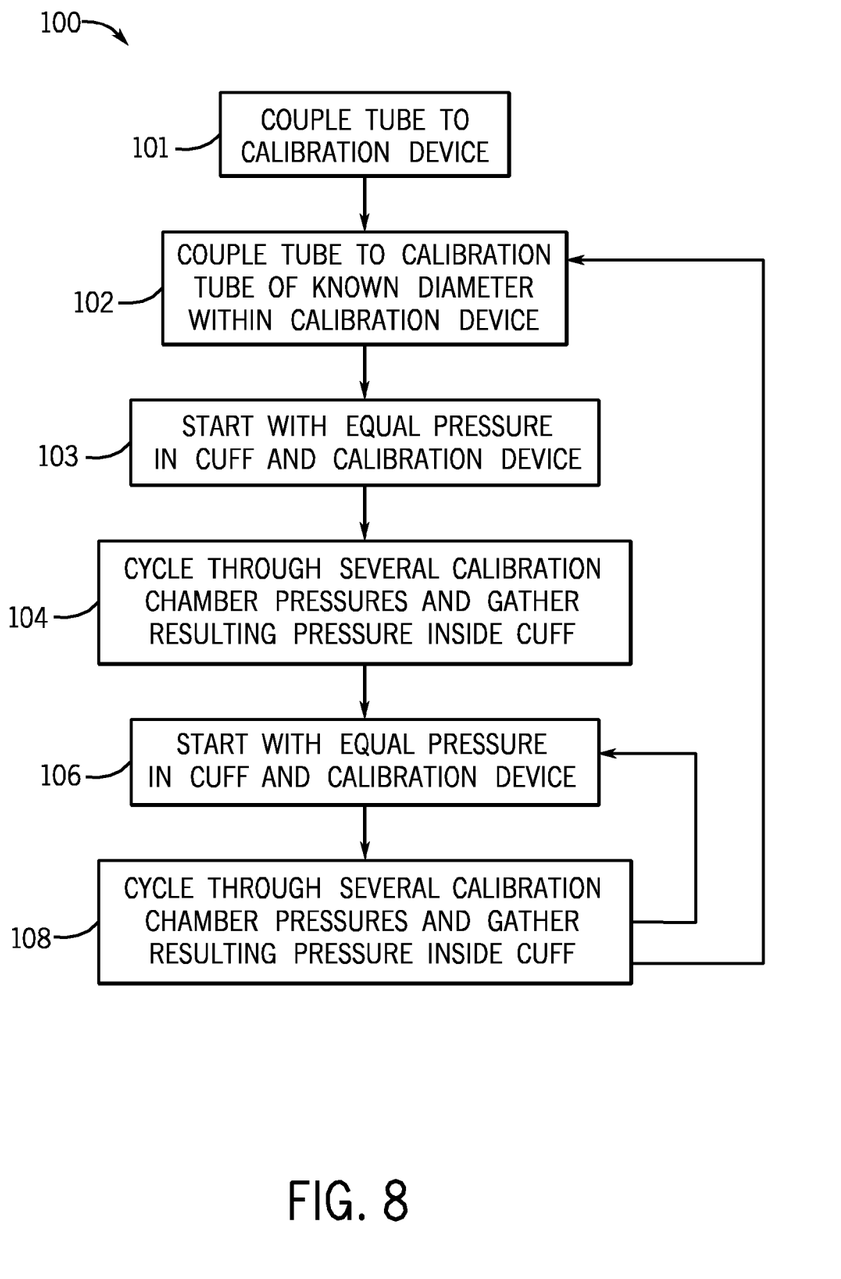
FIG. 8 is a flow diagram of another exemplary method for deriving calibration factors for a method involving measuring pressure through a primary cuff.

For calibration information relating to a cuff 14 that contacts a trachea, the calibration information may take the form of a family of empirically determined calibration curves, with each curve relating to a particular cuff/tube combination within a particular tracheal diameter. The family may involve curves for a number of different tracheal diameters. FIG. 8 is a process flow diagram illustrating a method for determination of such information for a cuff 14. The method is generally indicated by reference number 100 and includes various steps or actions represented by blocks. At step 101, a tracheal tube is coupled to a calibration device that may include a pressurized chamber and a plurality of model tracheas of different diameters. At step 102, a tracheal tube is inserted into a model trachea (e.g., a glass or acrylic tube) of a given diameter and coupled to a device that is capable of inflating the attached cuff 14 over a series of inflation pressures within the model trachea of a given size. At step 103, the cuff 14 and the device may be set so that the pressures are substantially equal. At step 104, the pressurized chamber is cycled through a range of pressures and measurements of the cuff pressure are taken, for example at predetermined increments, via pressure transducer 16. At step 106, the pressure inside the cuff 14 and the calibration device may be reset to equal pressure, starting at an incrementally larger cuff pressure as compared to the pressure used in step 103. Pressure measurements inside the cuff 14 are taken while the calibration device is cycled through a range of pressures at step 108. The method 100 may loop back to step 106 any number of times to repeat the process at different starting equal pressures of the cuff 14 and the calibration device. The relationship information over a series of cuff pressures may be stored on a memory circuit associated with the tube 12 (or otherwise, as described above). The process may return to step 102 one or more times to repeat the process for the tube 12 for a model trachea of a different diameter. In this manner, the cuff 14 may be calibrated for a range of pressures inside the cuff 14 and the trachea as well as for a range of tracheal diameters.

Figure 9:
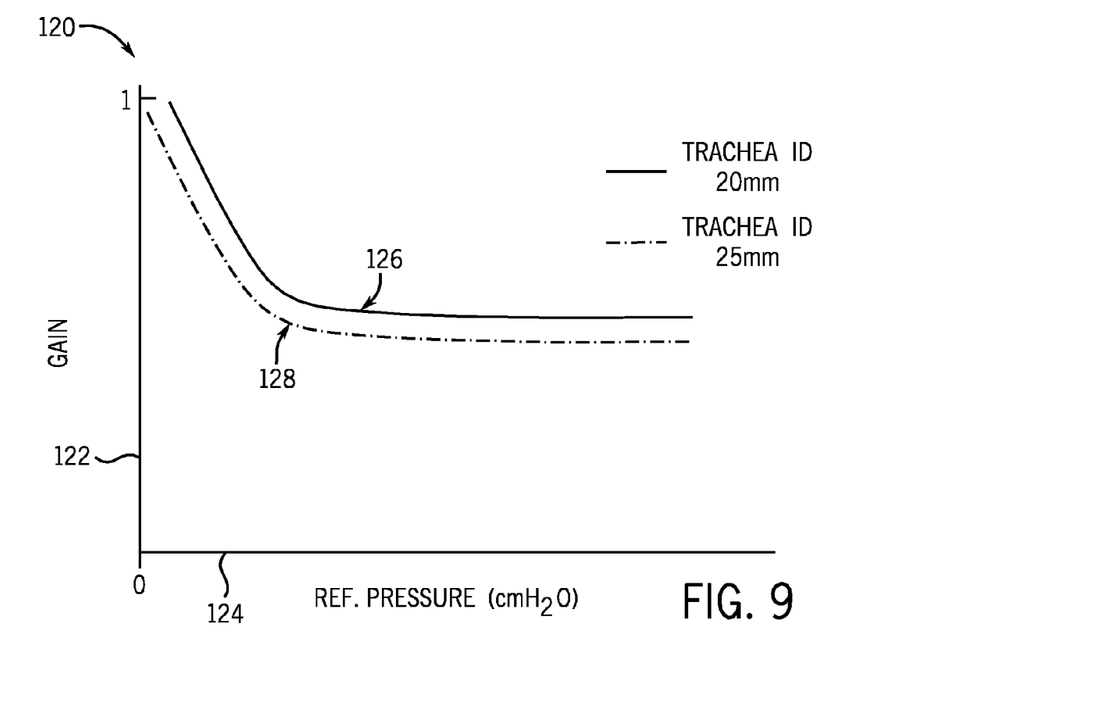
FIG. 9 is a plot of a family of calibration curves for a single cuff.

For example, FIG. 9 shows a plot of a family of calibration curves with the gain on the y-axis 122 and the reference pressure on the x-axis. The curves are specific to an individual tube 12 for different diameters of model tracheas. Curve 126 corresponds to a tracheal diameter of 20 mm while curve 128 corresponds to a tracheal diameter of 25 mm. A given tube size may be calibrated with model trachea of diameters corresponding to a recommended trachea range for that size. For example, a 7.5 mm tube may be recommended for use with trachea of diameters ranging from 20 mm-25 mm. Accordingly, the calibration information for a 7.5 mm tube may include a calibration curve at 20 mm and one at 25 mm and may also include curves for intervening tracheal sizes in that range.

The tube 12 may be inserted into a patient and the information stored on the memory circuit may be accessed. While the diameter of a patient's trachea may not be known, comparing the reading of airway pressure directly after intubation to the measured cuff pressure should allow a monitor 30 to select the appropriate curve. The airway pressure should be relatively close to (e.g., within 2% of) the tracheal pressure at early points in the intubation life of the cuff 14, before any buildup has accumulated on the tube 12. Based on the measured pressure in the cuff and the airway pressure, the monitor 30 may select the trachea surface corresponding to a closest tracheal diameter for the individual patient, or may interpolate between two tracheal inner diameter curves. The selected curve may then be used for the entire intubation with that tube 12 for that patient.

The above calibration techniques assume that the gain for each individual cuff/tube combination is linear over a range of pressures. In certain embodiments, such an assumption may have a negligible impact on the calculated trachea pressure (e.g., less than 10% variation from actual trachea pressure when assuming the gain is linear). However, the relationship between the gain of a particular cuff and the cuff pressure may be more complex, and the complexity may be accounted for when calculating the trachea pressure based on measured pressure inside a cuff.

Figure 10:
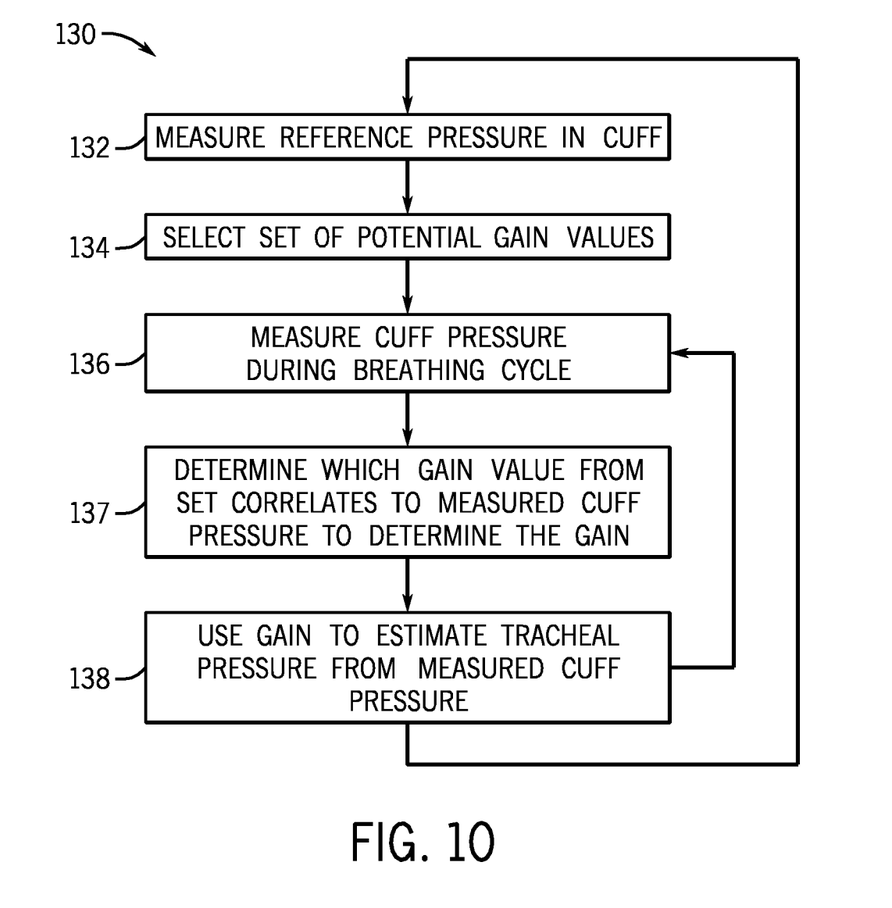
FIG. 10 is a flow diagram of another exemplary method for deriving calibration factors for a method involving measuring pressure through a secondary cuff.
Figure 11:
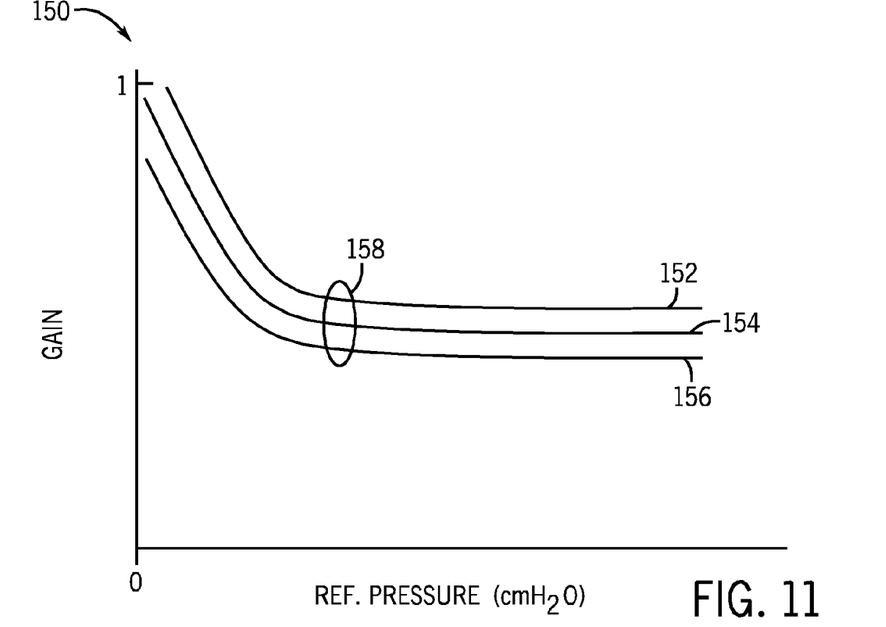
FIG. 11 is a plot of exemplary calibration curves for a secondary cuff.

For the case of a secondary cuff 50 that is assumed not to contact the walls of the trachea, a calculation that may take into account variations in gain over a range of cuff pressures is illustrated by the method 130 shown in FIG. 10. At step 132, a reference pressure, the $P_{CUFF\ (REFERENCE)}$, may be obtained by measuring the pressure in the inflated cuff 50 at expiration. At step 134, the $P_{CUFF\ (REFERENCE)}$ may be used to select a set of potential gain values. For example, such values may be selected from a plot 150 of gain curves (shown as curves 152, 154, and 156) shown in FIG. 11, that correspond to the particular tube/cuff combination. The plot 150 shown is a plot of gain on the y-axis and $P_{CUFF\ (REFERENCE)}$ on the x-axis. The set of gain values 158, each of which represents a different gain, may correspond to particular $P_{CUFF}$ pressures during the breath cycle. At step 136, the $P_{CUFF}$ pressure during the breath cycle may be sampled. From the measured $P_{CUFF}$ pressure, the gain is selected from the set of points 158 at step 137. After the gain is know, the tracheal pressure may be estimated as discussed herein at step 138. The method 130 may cycle between steps 136 and 138. In one embodiment, the method 130 may also return to step 132 to reestablish the $P_{CUFF\ (REFERENCE)}$ at any point during respiration of the patient. The information in the gain curves 152, 154, and 156 (which may be any suitable number of curves) is collected during calibration of the cuff 50. For example, the measured P CUFF (REFERENCE) may be measured as 20 cm $H_2O$. The gain points (e.g., points on the plot 150 corresponding to 20 cm $H_2O$) may represent different inflation pressures of the cuff 50 gathered while the calibration device chamber was set to a tracheal pressure corresponding to the $P_{CUFF\ (REFERENCE)}$ of 20 cm $H_2O$. Further, the correspondence of the gain values 158 to measured $P_{CUFF}$ pressures may also be established during calibration. The correspondence of the calibration information (e.g., the gain values) to the measured $P_{CUFF}$ pressures may be calculated from a previously determined (and/or stored) function, or may be established by using a lookup table or plot.

Figure 12:
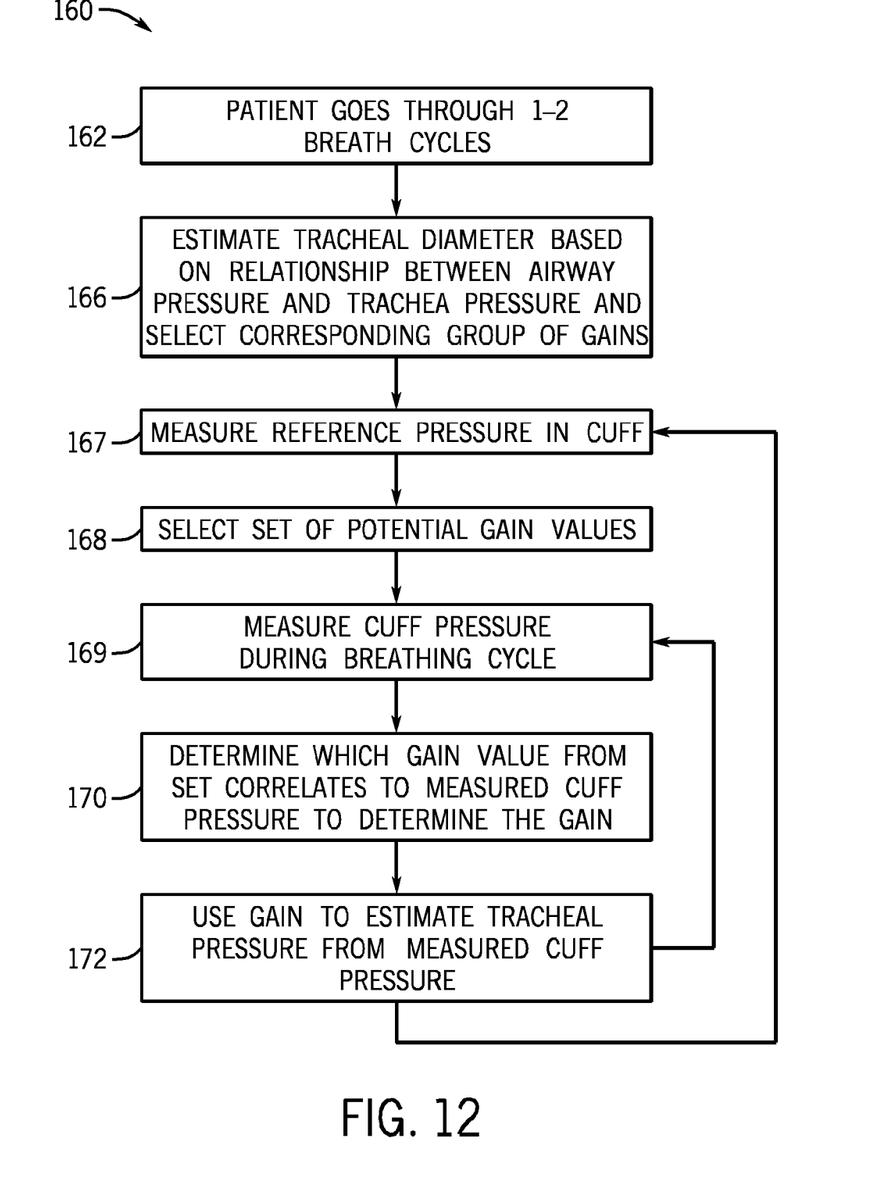
FIG. 12 is a flow diagram of another exemplary method for deriving calibration factors for a method involving measuring pressure through a primary cuff.

For the case of a cuff 14 that is inflated to contact the walls of the trachea, a calculation that may take into account variations in gain over a range of cuff pressures is illustrated by the method 160 shown in FIG. 12. At step 162, which may take place directly after intubation, a patient may go through at least one-two breath cycles.

Figure 13:
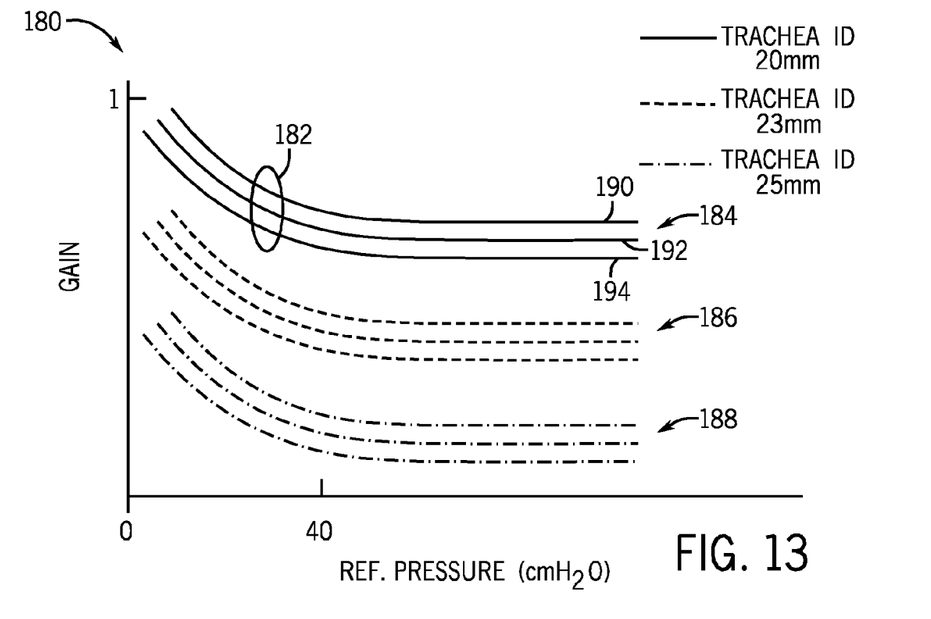
FIG. 13 is a plot of exemplary calibration curves for a primary cuff.

The relationship between the pressure at the ventilator and the pressure in the trachea may be expressed as $P_{TRACHEA} = P_{VENT}/\alpha$. The pressure in the airway at the ventilator may be used to estimate the tracheal pressure (where $\alpha$ is a constant that is known and may be stored by the tube 12 or the monitor 30). Once tracheal pressure is determined, the $P_{CUFF}$ pressure may be used at step 166 to estimate the tracheal diameter and select from among groups of gain curves. At this point, the $P_{CUFF\ (REFERENCE)}$ may be sampled at step 167. Using the $P_{CUFF\ (REFERENCE)}$, the set 182 of gain values may be selected at step 168 from the plot 180, shown in FIG. 13, of groups of gain curves, whereby each group is associated with a different tracheal diameter. As shown, group 184 is associated with 20 mm, group 186 is associated with 23 mm, and group 188 is associated with 25 mm. When the group is selected, for example group 184, the set 182 may correspond to particular $P_{CUFF}$ pressures for the cuff 14 during the breath cycle. At step 169, the $P_{CUFF}$ pressure during the breath cycle may be sampled. From the measured $P_{CUFF}$ pressure, the gain is selected from the set of points 182 at step 170 and the trachea pressure is determined at step 172 based on the gain and the $P_{CUFF}$ pressure as discussed herein. Curves 190 192, and 194 represent the gains at different calibration pressures for a single tracheal diameter. As in the calibration for the secondary cuff 50, the method 160 may cycle between steps 169 and 172. In one embodiment, the method 160 may also return to step 167 to reestablish the $P_{CUFF\ (REFERENCE)}$ at any point during respiration of the patient. Further, the calibration information for the cuff 14 may be collected, stored, and processed as provided herein.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of tracheal tube pressure, but these techniques may also be utilized for the measurement and/or analysis of the cuff pressure for any medical device inserted into a patient's airway. Rather, the various embodiments may cover all modifications, equivalents, and alternatives falling within the spirit and scope of the disclosure as defined by the following appended claims.

What is claimed is:

1. A monitor for determining trachea pressure comprising:
    a memory storing instructions configured to:
    determine a monitored cuff pressure in an inflated cuff of a tracheal tube disposed in the trachea of a subject;
    select a relationship from a plurality of relationships between the monitored cuff pressure and the trachea pressure;
    determine the trachea pressure based upon the selected relationship;

determine a lung pressure from the tracheal pressure and an offset, wherein the offset is a reference cuff pressure; and a processor configured to execute the instructions.

2. The monitor of claim 1, wherein the selected relationship is a function of the monitored cuff pressure, and wherein the instructions are configured to determine a current cuff pressure during respiration of the subject, and determine the trachea pressure based upon the relationship and the current cuff pressure.

3. The monitor of claim 2, wherein the instructions for determining the trachea pressure comprise instructions for multiplying a sensed cuff pressure by a ratio of the empirically determined lung pressure to the cuff pressure determined by the selected relationship.

4. The monitor of claim 3, wherein the instructions for determining the lung pressure comprise instructions for subtracting a reference cuff pressure from the product of the sensed cuff pressure and the ratio.

5. The monitor of claim 1, wherein the instructions for determining the lung pressure comprise an algorithm that implements an equation generally of the form:

$$P_T = rP_{Cs} - P_{Co},$$

wherein $P_T$ is the trachea pressure, $P_{Cs}$ is a cuff pressure monitored during respiration of the subject, $P_{Co}$ is the reference cuff pressure, and r is a ratio of the lung pressure to a sensed cuff pressure.

6. The monitor of claim 5, wherein the ratio is a non-constant value.

7. The monitor of claim 6, wherein the ratio varies with the monitored cuff pressure, and wherein the memory storage unite determines the current cuff pressure during respiration of the subject and determines the ratio based upon the monitored cuff pressure.

8. The monitor of claim 6, wherein the ratio is a function of a relationship between the tracheal tube and the trachea of the subject.

9. The monitor of claim 1, wherein the reference cuff pressure is the initial pressure of the cuff or the lowest trachea pressure seen in the breathing cycle after ventilation has begun.

10. The monitor of claim 1, wherein the monitor is coupled to a tracheal tube comprising a conduit configured to be inserted into the trachea of a patient, wherein the tracheal tube comprises:

an inflatable cuff coupled to the conduit;

a pressure transducer disposed within the inflatable cuff; and an information element comprising a memory circuit configured to store the plurality of relationships between the monitored cuff pressure and the trachea pressure.

11. The monitor of claim 10, wherein the inflatable cuff is configured to contact the trachea of the patient when inserted.

12. The monitor of claim 10, wherein the memory circuit is disposed on a connection or cable configured to couple the tracheal tube with the monitor.

13. The monitor of claim 1, wherein the selected relationship comprises a calibration factor representative of a physical characteristic of an inflatable cuff coupled to a conduit of a tracheal tube.

14. The monitor of claim 1, wherein the selected relationship comprises a calibration factor representative of a physical characteristic of a tracheal tube.

15. The monitor of claim 1, wherein the relationship is determined by selecting a point on a calibration curve representative of a reference inflation pressure of an inflatable cuff coupled to a conduit of a tracheal tube and disposed in the trachea of a patient.

16. The monitor of claim 1, comprising a display configured to display the lung pressure.

* * * * *